US00PP15921P2

(12) United States Plant Patent
Kabbes

(10) Patent No.: US PP15,921 P2
(45) Date of Patent: Aug. 16, 2005

(54) *AGASTACHE* PLANT NAMED 'AFTER EIGHT'

(50) Latin Name: *Agastache rugosa×Agastache foeniculum*
Varietal Denomination: After Eight

(75) Inventor: Brian Kabbes, Suameer (NL)

(73) Assignee: Inspiration Plant CV, Lisse (NL)

( * ) Notice: Subject to any disclaimer, the term of this patent is extended or adjusted under 35 U.S.C. 154(b) by 36 days.

(21) Appl. No.: 10/624,102

(22) Filed: Jul. 21, 2003

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM, Plant Variety Database, 204/02, GTI Jouve Retrieval Software, Citation for *Agastache* 'After Eight'.*

*Agastache* 'Blue Fortune' [online], [retrieved on May 19, 2004]. Tetrieved from the Internet: <http://www.noble-plants.com/introductions/agastache%20'blue%20forrtune'.htm>.*

Heritage Perennial profile [online], [retrieved on May 19, 2004]. *Agastache* 'Blue Fortune'. Retrieved from the Internet: <http://www.perennials.com/seedplant.html?item=1.025.30>.*

UPOV–ROM GTITM, Plant Variety Database, 2004/04, GTI Jouve Retrieval Software, Citation for *Agastache* 'After Eight'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Agastache* plant named 'After Eight', characterized by its upright, mounded and compact plant habit; freely flowering habit with numerous spikes per plant and numerous flowers per spike; and violet blue-colored flowers.

1 Drawing Sheet

Botanical classification/cultivar designation: *Agastache rugosa×Agastache foeniculum* cultivar After Eight.

BACKGROUND OF THE INVENTION

The present Invention relates to a new and distinct cultivar of *Agastache* plant, botanically known as *Agastache rugosa×Agastache foeniculum*, and hereinafter referred to by the name 'After Eight'.

The new *Agastache* is a product of a planned breeding program conducted by the Inventor in Suameer, The Netherlands. The new *Agastache* was discovered and selected by the Inventor in a seed bed of sown *Agastache* seed from various cross-pollinations of unnamed *Agastache rugosa* seedling selections, not patented, with unnamed *Agastache foeniculum* seedling selections, not patented, in a controlled environment in Suameer, The Netherlands in 1996. The new *Agastache* was selected as an individual seedling within the progeny of these various cross-pollinations on the basis of its violet blue-colored flowers.

Asexual reproduction of the new cultivar by vegetative cuttings at Suameer, The Netherlands, has shown that the unique features of this new *Agastache* are stable and reproduced true to type in successive generations.

SUMMARY OF THE INVENTION

Plants of the cultivar After Eight have not been observed under all possible environmental conditions. The phenotype may vary somewhat with variations in environment such as temperature and light intensity without, however, any variance in genotype.

The following traits have been repeatedly observed and are determined to be the unique characteristics of 'After Eight'. These characteristics in combination distinguish 'After Eight' as a new and distinct *Agastache* cultivar:

1. Upright, mounded and compact plant habit.
2. Freely flowering habit with numerous spikes per plant and numerous flowers per spike.
3. Violet blue-colored flowers.

Plants of the new *Agastache* are similar to plants of the parent selections. Compared to plants of the parent selections, plants of the new *Agastache* are more compact, have deeper violet blue flower coloration, and flower for a longer period of time.

Plants of the new *Agastache* can also be compared to plants of the *Agastache* cultivar Blue Fortune, not patented. Compared to plants of the cultivar Blue Fortune, plants of the new *Agastache* are more compact, flower for a longer period of time and have darker violet blue-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Agastache*.

The photograph on the right side of the sheet comprises a side perspective view of a typical flowering plant of 'After Eight' grown in a outdoor nursery.

The photograph on the left side of the sheet is a close-up view of typical flowering spikes of 'After Eight'.

DETAILED BOTANICAL DESCRIPTION

Plants shown in the aforementioned photographs and used in the following description were grown under conditions which closely approximate commercial production conditions during the spring and summer in an outdoor nursery in Suameer, The Netherlands. Plants in the photographs and those used for the description were about one year old when the photographs and description were taken. In the following description, color references are made to The Royal Horticultural Society Colour Chart, 1995 Edition, except where general terms of ordinary dictionary significance are used.

Botanical classification: *Agastache rugosa*×*Agastache foeniculum* cultivar After Eight.

Parentage:

*Female, or seed, parent.*—Unnamed *Agastache rugosa* seedling selections, not patented.

*Male, or pollen, parent.*—Unnamed *Agastache foeniculum* seedling selections, not patented.

Propagation:

*Type.*—By vegetative cuttings.

*Time to initiate and develop roots.*—About 14 days during the spring under outdoor production conditions, about 15° C.

*Root description.*—Numerous; fine.

Plant description:

*Form.*—Perennial. Upright, mounded and compact plant habit; broad inverted triangle. Flowering stems arise from the roots; moderate branching from the stems, typically about six to eight lateral branches per plant; dense and bushy plant habit; moderate to vigorous growth habit. Freely flowering with numerous flowering spikes per plant and numerous flowers arranged in verticillasters on crowded spikes.

*Plant height.*—About 45 cm.

*Plant width.*—About 35 to 45 cm.

*Stem description.*—Diameter: About 3 mm. Internode length: About 6 to 15 cm. Strength: Strong. Texture: Smooth, glabrous. Color: Towards the base, 165A; towards the apex, 183C.

*Foliage description.*—Arrangement: Opposite, simple. Length: About 4 to 6.5 cm. Width: About 1.8 to 3 cm. Shape: Lanceolate to ovate. Apex: Acute. Base: Obtuse. Margin: Serrate. Texture, upper and lower surfaces: Smooth, glabrous. Venation pattern: Pinnate. Fragrance: When rubbed, strong peppermint scent. Color: Developing foliage, upper surface: 147A; venation, 147A. Developing foliage, lower surface: 183A; venation, 184B. Fully expanded foliage, upper surface: 144A; venation, 144A. Fully expanded foliage, lower surface: 137D; venation, 147C. Petiole length: About 1 to 2.5 cm. Petiole diameter: About 1.5 to 2 mm. Petiole color, developing foliage: 183C. Petiole color, fully expanded foliage: 165A.

Flower description:

*Flower arrangement and shape.*—Numerous single labiate flowers arranged in verticillasters on terminal spikes; flowers face mostly outwardly. Freely flowering, about 1,200 to 1,500 flowers and flower buds per plant; about 200 flowers and flower buds develop per flower spike.

*Natural flowering season.*—Continuous flowering from the late spring through fall in The Netherlands.

*Flower longevity on the plant.*—Individual flowers last about one week on the plant. Flowers not persistent.

*Fragrance.*—When rubbed, strong peppermint scent.

*Flower buds (about one day before opening).*—Length: About 0.5 mm. Diameter: About 2 mm. Shape: Obovate. Color: 86B.

*Flower spike length.*—About 10 cm.

*Flower spike diameter.*—About 3 cm.

*Flower diameter.*—About 7 to 9 mm.

*Flower depth (height).*—About 5 mm.

*Petals.*—Arrangement: Labiate; corolla two lipped, upper lip erect with two lobes, lower lip with three lobes; lips fused at the base. Length: About 7 to 9 mm. Shape: Oblanceolate. Apex: Acute to obtuse. Margin: Entire. Texture, upper and lower surfaces: Smooth, glabrous. Color: When opening and fully opened, upper surface: 97A. When opening and fully opened, lower surface: 97A.

*Sepals.*—Arrangement: Five sepals fused into a tube. Calyx length: About 4 to 5 mm. Calyx width: About 2 mm. Apex: Acuminate. Margin: Entire. Texture, upper and lower surfaces: Smooth, glabrous. Color, upper and lower surfaces: 86A.

*Peduncles.*—Strength: Strong. Length: About 15 to 45 cm. Diameter: About 3 mm. Aspect: Mostly erect. Texture: Smooth. Color: 183C.

*Pedicels.*—Strength: Moderately strong. Length: About 1 to 2 mm. Diameter: Less than 1 mm. Aspect: About 40 to 50° from vertical. Texture: Smooth. Color: 69C.

*Reproductive organs.*—Stamens: Quantity per flower: About four. Anther attachment: Dorsifixed. Anther length: About 0.7 to 1 mm. Anther color: 97A. Pollen amount: Sparse. Pollen color: 11A. Pistils: Quantity per flower: One. Pistil length: About 0.7 to 0.9 mm. Stigma shape: Three-parted; recurved. Stigma color: 96A. Style length: About 0.7 to 0.9 mm. Style color: 97A. Ovary color: 72C.

*Fruit.*—Type: Nutlet. Shape: Round. Length: About 1 mm. Diameter: About 1 mm. Color: Close to 202A.

*Seed.*—Length: Less than 1 mm. Diameter: Less than 1 mm. Color: Close to 202A.

Disease/pest resistance: Plants of the new *Agastache* have not been noted to be resistant to pathogens and pests common to *Agastache*.

It is claimed:

1. A new and distinct cultivar of *Agastache* plant named 'After Eight', as illustrated and described.

* * * * *

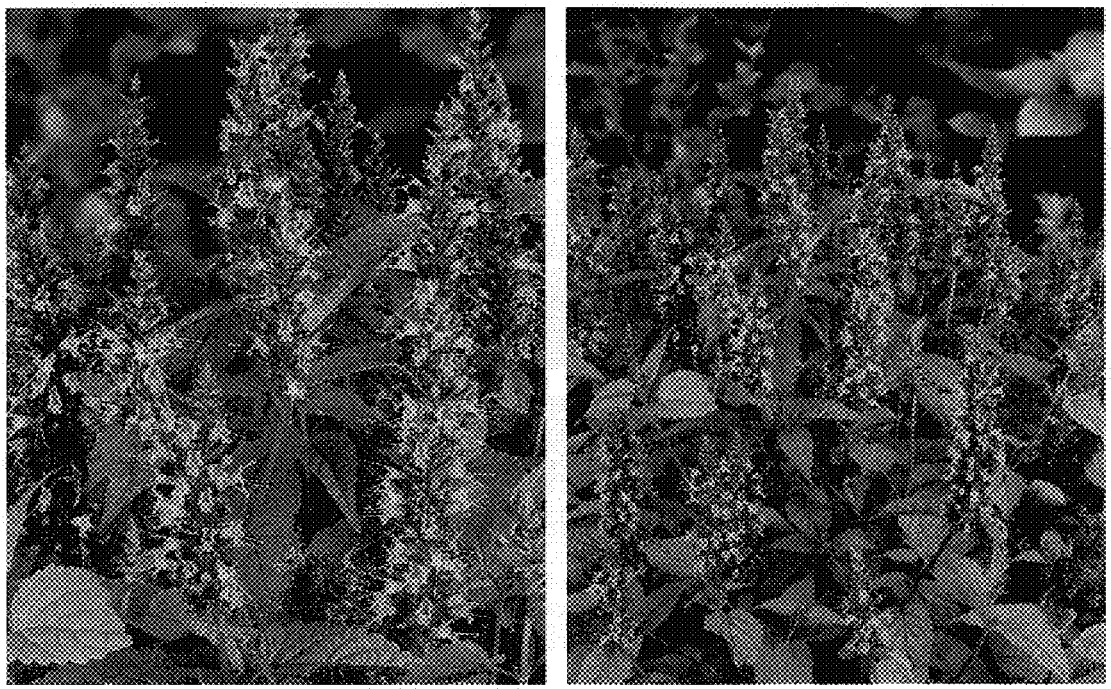
After Eight